United States Patent [19]

Bernardin

[11] Patent Number: 4,994,037
[45] Date of Patent: Feb. 19, 1991

[54] ABSORBENT STRUCTURE DESIGNED FOR ABSORBING BODY FLUIDS

[75] Inventor: Leo J. Bernardin, Appleton, Wis.

[73] Assignee: Kimberly-Clark Corporation, Neenah, Wis.

[21] Appl. No.: 550,239

[22] Filed: Jul. 9, 1990

[51] Int. Cl.⁵ ............................................. A61F 13/16
[52] U.S. Cl. .................................. 604/368; 604/378
[58] Field of Search ............... 604/367, 368, 374–380, 604/385.1, 385.2

[56] References Cited

U.S. PATENT DOCUMENTS

| | | | |
|---|---|---|---|
| Re. 30,057 | 7/1989 | Schaar | 128/287 |
| Re. 32,649 | 4/1988 | Brandt et al. | 604/368 |
| 2,750,944 | 6/1956 | Tollstrup | 128/290 |
| 2,788,003 | 6/1955 | Morin | 128/284 |
| 2,952,260 | 9/1960 | Burgeni | 128/290 |
| 2,955,641 | 10/1960 | Burgeni | 154/33 |
| 3,017,304 | 1/1962 | Burgeni | 154/54 |
| 3,060,936 | 10/1962 | Burgeni | 128/290 |
| 3,339,550 | 9/1967 | Van Haaften | 128/290 |
| 3,364,931 | 1/1968 | Hirsch | 128/290 |
| 3,441,023 | 4/1969 | Rijssenbeek | 128/287 |
| 3,441,024 | 4/1969 | Ralph | 128/287 |
| 3,494,362 | 2/1970 | Burgeni | 128/290 |
| 3,528,421 | 9/1970 | Vaillancourt | 128/284 |
| 3,545,441 | 12/1970 | Gravdahl | 128/284 |
| 3,592,194 | 7/1971 | Duncan | 128/287 |
| 3,612,055 | 10/1971 | Mesek et al. | 128/287 |
| 3,654,929 | 4/1972 | Nilsson et al. | 128/287 |
| 3,661,154 | 5/1972 | Torr | 128/284 |
| 3,669,103 | 6/1972 | Harper et al. | 128/156 |
| 3,670,731 | 6/1972 | Harmon | 128/284 |
| 3,683,916 | 8/1972 | Mesek et al. | 128/287 |
| 3,757,785 | 9/1973 | Wosaba, II | 128/287 |
| 3,763,863 | 10/1973 | Mesek et al. | 128/287 |
| 3,783,872 | 1/1974 | King | 128/290 R |
| 3,814,101 | 6/1974 | Kozak | 128/287 |
| 3,886,941 | 6/1975 | Duane et al. | 128/287 |
| 3,888,257 | 6/1975 | Cook et al. | 128/296 |
| 3,901,236 | 8/1975 | Assarsson et al. | 128/284 |
| 3,903,889 | 9/1975 | Torr | 128/287 |
| 3,908,659 | 9/1975 | Wehrmeyer et al. | 128/287 |

(List continued on next page.)

FOREIGN PATENT DOCUMENTS

| | | |
|---|---|---|
| 20413/70 | 8/1970 | Australia . |
| 57316/73 | 6/1973 | Australia . |
| 506555 | 8/1976 | Australia . |
| 63587/80 | 10/1979 | Australia . |
| 77648/81 | 12/1980 | Australia . |
| 91332/82 | 12/1981 | Australia . |

(List continued on next page.)

OTHER PUBLICATIONS

Article entitled "Liquid Advance in Layered Fibrous Composites," Authors H. V. Nguyen and D. F. Durso.

Primary Examiner—C. Fred Rosenbaum
Assistant Examiner—Sharon Rose

[57] ABSTRACT

In a disposable absorbent garment, an absorbent structure includes liquid absorbing material comprising an upper layer comprising preferably softwood fibers and having a density from about 0.03 to about 0.14 g/cc, a lower layer comprising preferably hardwood fibers, formed substantially separately from and underlying at least a portion of the upper layer, the second layer having top and bottom surfaces, a density from about 0.14 to about 0.3 g/cc, a total void volume greater than about 80%, an average pore size distribution generally less than the average pore size distribution of the upper layer. There is an overlap in the pore size distributions of the upper and lower layers such that the smallest pores in the upper layer are smaller than the largest pores in the lower layer and front and rear fluid storage pouches, preferably spaced from one another at the front one-third and rear one-third of the absorbent structure, respectively, each pouch comprise superabsorbent material disposed in a hydrophilic web. The spaced fluid storage pouches are preferably located underlying the bottom surface of the lower layer so that the absorbent structure is substantially free of superabsorbent material in the middle one-third thereof.

48 Claims, 12 Drawing Sheets

U.S. PATENT DOCUMENTS

| | | | |
|---|---|---|---|
| 3,916,900 | 11/1975 | Breyer et al. | 128/287 |
| 3,934,588 | 1/1976 | Mesek et al. | 128/290 |
| 3,938,522 | 2/1976 | Repke | 128/287 |
| 3,968,798 | 7/1976 | Hokanson | 128/284 |
| 3,993,820 | 11/1976 | Repke | 428/167 |
| 3,996,936 | 12/1976 | Widlund et al. | 128/287 |
| 4,022,210 | 5/1977 | Glassman | 128/284 |
| 4,027,672 | 6/1977 | Karani | 128/284 |
| 4,029,100 | 6/1977 | Karami | 128/284 |
| 4,043,952 | 8/1977 | Ganslau et al. | 260/17.4 ST |
| 4,047,531 | 9/1977 | Karami | 604/378 |
| 4,055,180 | 10/1977 | Karami | 604/378 |
| 4,087,506 | 5/1978 | Cook et al. | 264/112 |
| 4,090,013 | 5/1978 | Ganslau et al. | 526/15 |
| 4,102,340 | 7/1978 | Mesek et al. | 128/287 |
| 4,103,062 | 7/1978 | Aberson et al. | 428/283 |
| 4,105,033 | 8/1975 | Chatterjee et al. | 128/285 |
| 4,144,886 | 3/1979 | Holst et al. | 128/284 |
| 4,166,464 | 9/1979 | Korpman | 128/287 |
| 4,186,165 | 1/1980 | Aberson et al. | 264/112 |
| 4,212,302 | 7/1980 | Karami | 128/287 |
| 4,213,459 | 7/1980 | Sigl et al. | 128/287 |
| 4,223,677 | 9/1980 | Anderson | 128/287 |
| 4,232,674 | 11/1980 | Melican | 128/287 |
| 4,235,237 | 11/1980 | Mesek et al. | 128/284 |
| 4,247,362 | 1/1981 | Williams | 162/13 |
| 4,259,387 | 3/1981 | Mesek | 428/167 |
| 4,259,958 | 4/1981 | Goodbar | 128/287 |
| 4,260,443 | 4/1981 | Lindsay et al. | 156/220 |
| 4,269,188 | 5/1981 | Nishizawa et al. | 128/287 |
| 4,282,874 | 8/1981 | Mesek | 128/287 |
| 4,295,987 | 10/1981 | Parks | 252/194 |
| 4,327,728 | 5/1982 | Elias | 128/285 |
| 4,327,729 | 5/1982 | King | 128/287 |
| 4,333,462 | 6/1982 | Holtman et al. | 128/287 |
| 4,333,463 | 6/1982 | Holtman | 128/287 |
| 4,333,464 | 6/1982 | Nakano | 128/290 |
| 4,338,371 | 7/1982 | Dawn et al. | 428/283 |
| 4,340,057 | 7/1982 | Block et al. | 128/284 |
| 4,340,706 | 7/1982 | Obayashi et al. | 526/207 |
| 4,354,901 | 10/1982 | Kopolow | 162/158 |
| 4,364,992 | 12/1982 | Ito | 428/283 |
| 4,381,782 | 5/1983 | Mazurak et al. | 604/368 |
| 4,381,783 | 5/1983 | Elias | 604/368 |
| 4,397,644 | 8/1983 | Matthews et al. | 604/378 |
| 4,410,324 | 10/1983 | Sabee | 604/368 |
| 4,411,660 | 10/1983 | Dawn et al. | 604/396 |
| 4,413,996 | 11/1983 | Taylor | 604/382 |
| 4,417,893 | 11/1983 | Mizutani et al. | 604/366 |
| 4,424,247 | 1/1984 | Erickson | 428/138 |
| 4,433,972 | 2/1984 | Malfitano | 604/385 |
| 4,449,979 | 5/1984 | Holtman | 604/379 |
| 4,461,621 | 7/1984 | Karami et al. | 604/368 |
| 4,468,428 | 8/1984 | Early et al. | 428/221 |
| 4,480,000 | 10/1984 | Watanabe et al. | 428/284 |
| 4,496,358 | 1/1985 | Karami et al. | 604/379 |
| 4,500,315 | 2/1985 | Pieniak et al. | 604/379 |
| 4,501,586 | 2/1985 | Holtman | 604/380 |
| 4,501,587 | 2/1985 | Enloe | 604/385 |
| 4,531,945 | 7/1985 | Allison | 604/378 |
| 4,537,590 | 8/1985 | Pieniak et al. | 604/379 |
| 4,540,414 | 9/1985 | Wishman | 604/378 |
| 4,540,454 | 9/1985 | Pieniak et al. | 156/622 |
| 4,560,372 | 12/1985 | Pieniak | 604/369 |
| 4,573,986 | 3/1986 | Minetola et al. | 604/366 |
| 4,573,987 | 3/1986 | Lamb, Jr. | 604/378 |
| 4,573,988 | 3/1986 | Pieniak et al. | 604/379 |
| 4,585,448 | 4/1986 | Enloe | 604/378 |
| 4,605,401 | 8/1986 | Chmelir et al. | 604/368 |
| 4,643,726 | 2/1987 | Gegelys | 604/368 |
| 4,673,402 | 6/1987 | Weisman et al. | 604/368 |
| 4,685,915 | 8/1987 | Hasse et al. | 604/378 |
| 4,695,278 | 9/1987 | Lawson | 604/385 A |
| 4,699,619 | 10/1987 | Bernardin | 604/378 |
| 4,699,620 | 10/1987 | Bernardin | 604/385 A |
| 4,704,116 | 11/1987 | Enloe | 604/385 A |
| 4,731,065 | 3/1988 | Yamada | 604/355 |
| 4,731,071 | 3/1988 | Pigneul | 604/385 R |
| 4,738,677 | 4/1988 | Foreman | 604/385 R |
| 4,743,246 | 5/1988 | Lawson | 604/385 A |
| 4,753,646 | 6/1988 | Enloe | 604/385 R |
| 4,764,325 | 8/1988 | Angstadt | 264/113 |
| 4,834,735 | 5/1989 | Alemany et al. | 604/368 |
| 4,838,885 | 6/1989 | Bernardin | 604/385.1 |
| 4,842,594 | 6/1989 | Ness | 604/368 |

FOREIGN PATENT DOCUMENTS

| | | |
|---|---|---|
| 65259/80 | 5/1984 | Australia |
| 59247/86 | 1/1987 | Australia |
| 60401/86 | 2/1987 | Australia |
| 1245001 | 11/1988 | Canada |
| 47042 | 11/1990 | China |
| 0108637 | 5/1984 | European Pat. Off. |
| 0160569 | 4/1985 | European Pat. Off. |
| 0158914 | 10/1985 | European Pat. Off. |
| 0160572 | 11/1985 | European Pat. Off. |

(List continued on next page.)

FOREIGN PATENT DOCUMENTS

| | | |
|---|---|---|
| 0228353 | 6/1986 | European Pat. Off. |
| 0254476 | 1/1988 | European Pat. Off. |
| 54-4500 | 1/1979 | Japan |
| 59-112004 | of 1984 | Japan |
| 63-99861 | 5/1988 | Japan |
| 80/01455 | 7/1980 | PCT Int'l Appl. |
| 1308935 | 3/1973 | United Kingdom |
| 1389891 | 4/1975 | United Kingdom |
| 1402327 | 8/1975 | United Kingdom |
| 1406615 | 9/1975 | United Kingdom |
| 1547524 | 6/1979 | United Kingdom |
| 2061115 | 4/1981 | United Kingdom |
| 2063683 | 6/1981 | United Kingdom |
| 2087240A | 6/1982 | United Kingdom |
| 2087731A | 6/1982 | United Kingdom |
| 2089214 | 6/1982 | United Kingdom |
| 2111836 | 7/1983 | United Kingdom |
| 2131346A | 6/1984 | United Kingdom |
| 2131699A | 6/1984 | United Kingdom |
| 2131700A | 6/1984 | United Kingdom |
| 2132897 | 7/1984 | United Kingdom |
| 2144995 | 3/1985 | United Kingdom |
| 2145661A | 4/1985 | United Kingdom |
| 2165757 | 4/1986 | United Kingdom |
| 2175024 | 11/1986 | United Kingdom |
| 2175212 | 11/1986 | United Kingdom |
| 2191515A | 12/1987 | United Kingdom |
| 2193625A | 2/1988 | United Kingdom |

ABSORBENT STRUCTURE DESIGNED FOR ABSORBING BODY FLUIDS

This application is a continuation of copending application Ser. No. 07/442,441 filed Nov. 22 1989, now abandoned, which is, in turn a continuation of copending application Ser. No. 07/081,449, filed on Aug. 4, 1987, now abandoned, which is in turn a continuation-in-part application of U.S. patent application Ser. No. 886,780, filed July 17, 1986, now U.S. Pat. No. 4,699,619 issued Oct. 13, 1987, which in turn is a continuation-in-part application of U.S. Ser. No. 656,384 filed Aug. 31, 1984, now abandoned, which in turn is a continuation-in-part application of U.S. Ser. No. 599,882, filed Apr. 13, 1984, now abandoned.

TECHNICAL FIELD

This invention is directed to an improved absorbent structure designed for use in absorbent pads such as diapers, for absorbing body fluids.

BACKGROUND OF THE INVENTION

This invention relates to an absorbent structure such as may be used in a disposable diaper, which is an improvement upon U.S. Pat. No. 4,699,619 issued Oct. 13, 1987, to Bernardin, upon which prior published British Application No. 2,165,757A and European Application No. 0158914 are based.

Disposable diapers generally include an inner, liquid permeable liner that lies closest to the wearer's skin. An outer, liquid impermeable cover is disposed at the outside of the diaper, furthest away from the wearer. In between the liner and the cover is a fibrous liquid absorbent material or batt.

In general, the most economical liquid absorbent material for use in disposable diapers is cellulosic fibers such as comminuted wood pulp, commonly known in the art as "fluff pulp," or simply "fluff." Batts made from these fibers have a low density and a high capacity for absorbing fluids, but their wicking ability is very poor. Thus, the low central crotch portion of the diaper as worn tends to become very wet when waste fluids are released thereupon, while the fluff included in the higher portions of the diaper (as worn) can remain dry with its absorbent capacity unused.

Several problems are posed by this. First, it is uneconomical to line a diaper with fluff, the majority of which will be wasted. Further, there can be leakage from the liquid saturated central portion of the diaper. Still further, this concentration of liquid localized in one region of the diaper can cause discomfort to the wearer of the diaper.

One prior art approach noted by Sigl in U.S. Pat. No. 4,213,459 to avoid some of these problems is to decrease the pore size such that the improved capillary action of the pores overcomes the force of gravity sufficiently to cause the waste liquid to move upwardly in the diaper. However, it has been noted that the total absorption capacity is reduced by reducing the average pore size. Nevertheless, the use of this approach to achieve a better distribution of fluid throughout the available area in the diaper has generally been the approach of choice despite the resulting loss in absorption capacity.

A further step was taken towards the solution of these problems by Sigl (in U.S. Pat. No. 4,213,459, assigned to the assignee of the present invention). Sigl discloses providing a localized area of increased density fluff in the batt for wicking waste fluid to a higher portion of the diaper. Although this presented an advance in the art, it was not without drawbacks. First, the surface of the diaper nearest the wearer's skin directly beneath the lining becomes soaked. Further, the only places where liquid could be transferred from the lower density material to the higher density material were at the borders or edges where the lower density material adjoins the higher density material. Thus, it was suggested in that patent that the areas around the densified region of the batt should remain undensified.

Prior published British patent applications Nos. 2,132,897 and 2,063,683 of Colgate-Palmolive each disclose diapers having multi-layered absorbent pads. The 2,132,897 reference disclosed spaced, lengthwise strips of hydrogel, coated upon and sandwiched between the surfaces of the pads.

Likewise, prior published British Patent Application Nos. 2,061,115, 2,089,214 and 2,111,836 of the instant assignee all disclose sanitary napkins having multi-layered absorbent pads.

Prior published British Patent Application Nos. 2,175,024A and 2,175,212A of Proctor & Gamble also disclose absorbent articles which either have a concentration of superabsorbent material in the back face half of a single pad or a discrete superabsorbent treated core underlying a top pad in the front of a diaper wherein urine is immediately excreted.

The prior art does not recognize that fluid can be distributed to remote areas of a diaper and retained remote from the crotch area of a wearer, as well as being retained in the immediate urination target zone.

The present invention provides a further advancement in the art, as will be fully explained below.

SUMMARY OF THE INVENTION

According to the invention, a disposable absorbent garment is provided of the type having an absorbent structure having opposed longitudinal ends, a central crotch portion and wherein there is included a body-facing sheet, a backing sheet and liquid absorbing material therebetween. The liquid absorbing material comprises a first layer comprising cellulosic fibers and having a density from about 0.03 to about 0.14 g/cc, said first layer having a top surface underlying the facing sheet and a bottom surface opposite from the top surface thereof.

A second layer comprising cellulosic fibers is formed substantially separately from and underlying at least a portion of said first layer, having top and bottom surfaces, a density from about 0.14 to about 0.3 g/cc, a total void volume greater than about 80% and an average pore size distribution generally less than the average pore size distribution of the first layer. There is an overlap in the pore size distributions of the first and second layers such that the smallest pores in the first layer are smaller than the largest pores in the second layer.

Front and rear fluid storage pouches each comprising superabsorbent material disposed in a hydrophilic web are located underlying the first layer and spaced from one another at the opposed longitudinal ends, respectively, of the absorbent structure.

In one preferred embodiment, the fluid storage pouches are disposed beneath the bottom surface of the second layer in fluid conductive contact therewith wherein a surface of the superabsorbent material is in contact with the bottom surface of the second layer.

In another preferred embodiment, the front and rear retention pouches are respectively disposed at the front one-third and rear one-third of the absorbent structure, the central crotch portion of the absorbent structure being substantially free of superabsorbent material.

In a further preferred embodiment, the first layer comprises softwood fibers and the second layer comprises hardwood fibers.

Objects and advantages of the invention will best be understood with reference to the following detailed description read in connection with the drawings.

DETAILED DESCRIPTION OF THE PREFERRED EMBODIMENT

Figure 1:
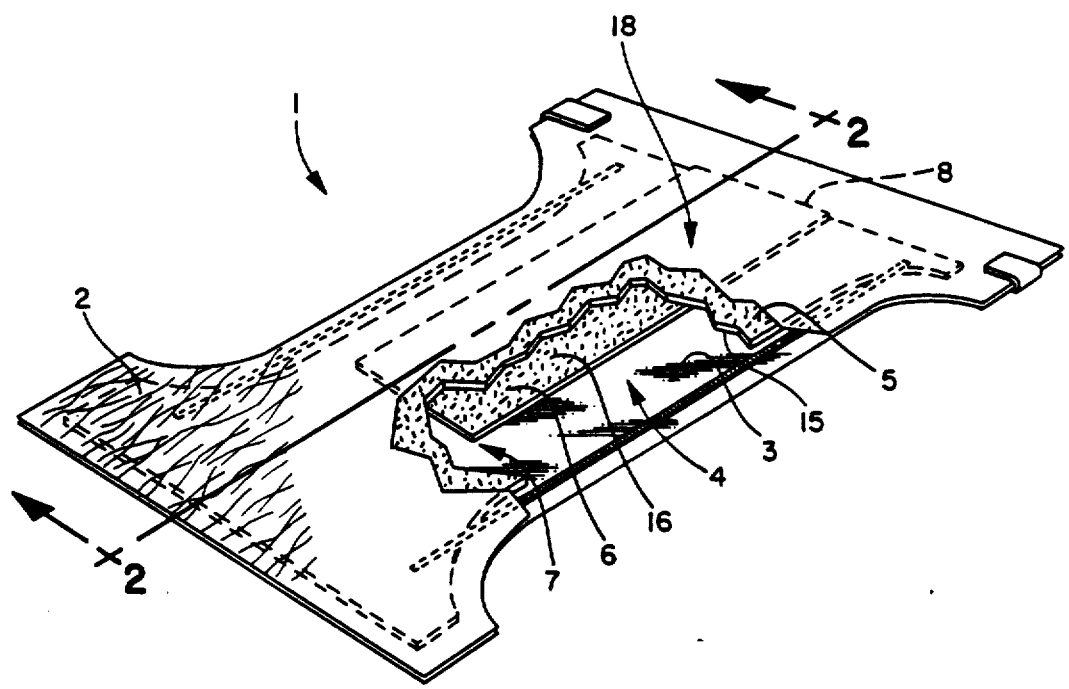
FIG. 1 is a perspective plan view of a first preferred embodiment of the invention without the superabsorbent material included therein.

Turning now to the drawings, the disposable diaper 1 in which the present invention is embodied comprises generally a body facing, liquid permeable liner 2, an outer liquid impermeable cover 3, and a liquid absorbing material indicated generally as 4 therebetween. The focus of this invention is directed to the liquid absorbing material 4. The liquid absorbing material 4 comprises a first, lower density layer 5 of cellulosic fibers such as comminuted wood pulp (fluff) which lies beneath the inner liner 2. A second, higher density layer 6 of fluff lies beneath at least a portion of the first lower density layer 5 such that waste fluid can be transferred from the lower density layer 5 to the higher density layer 6. Thus, a lower surface 15 of the lower density layer 5 should be contiguous with at least a portion of an upper surface 16 of the higher density layer 6. However, a tissue layer can be placed between the layers 5 and 6 without departing from the scope of this invention.

Predominantly softwood pulp fluff can be used for each of the layers 5 and 6. Alternatively, a layer of predominantly softwood fluff can be used for the layer 5 and a layer of preponderantly hardwood fluff can be used for the layer 6, in which case it is the average pore size and not necessarily the density that varies between the layers 5 and 6, as will shortly be explained. For the purposes of this disclosure and the accompanying claims, "predominantly" is intended to mean at least about 80% while "preponderantly" is intended to mean at least about 50%.

Figure 2:
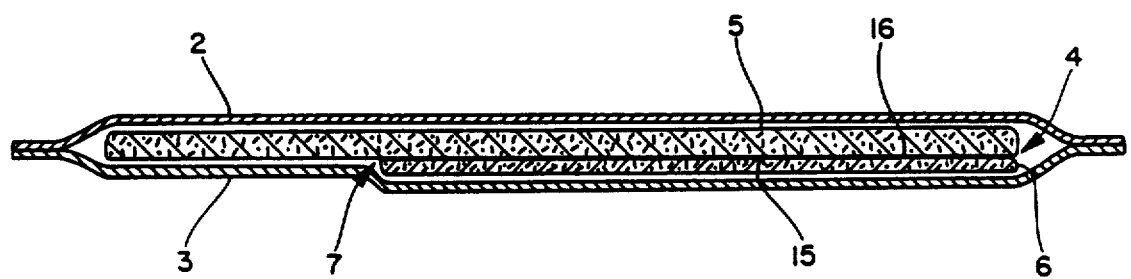
FIG. 2 is a longitudinal cross-sectional view taken along line 2—2 of FIG. 1.

In the first preferred embodiment shown in FIGS. 1 and 2, the higher density layer 6 is formed as a strip extending from a target area 7, where liquid waste will initially accumulate, to an upper edge 8 towards the back of the diaper. The higher density layer 6 draws waste fluid from the lower density layer 5 in the target area 7 upwardly towards the edge 8 at the back of the diaper 1. Further, along upper regions 18 of the higher density layer 6 towards the upper edge 8 there is, surprisingly, substantial fluid transfer back from the higher density layer 6 to the lower density layer 5. It is important to note that although this flowback occurs from the higher density layer 6 to the lower density layer 5, the lower density layer 5 only draws sufficient fluid to satisfy its unsaturated capillary forces proximate to the higher density layer 6, where there is an overlap in pore sizes such that the smallest pores in the lower density layer 5 are smaller than the largest pores in the higher density layer 6. The lower density layer 5 drains fluid from the higher density layer 6 but does not become soaked, with the advantage that the wearer's comfort is maintained while a significant proportion of the absorption capacity of the lower density layer 5 is utilized.

Figure 3:
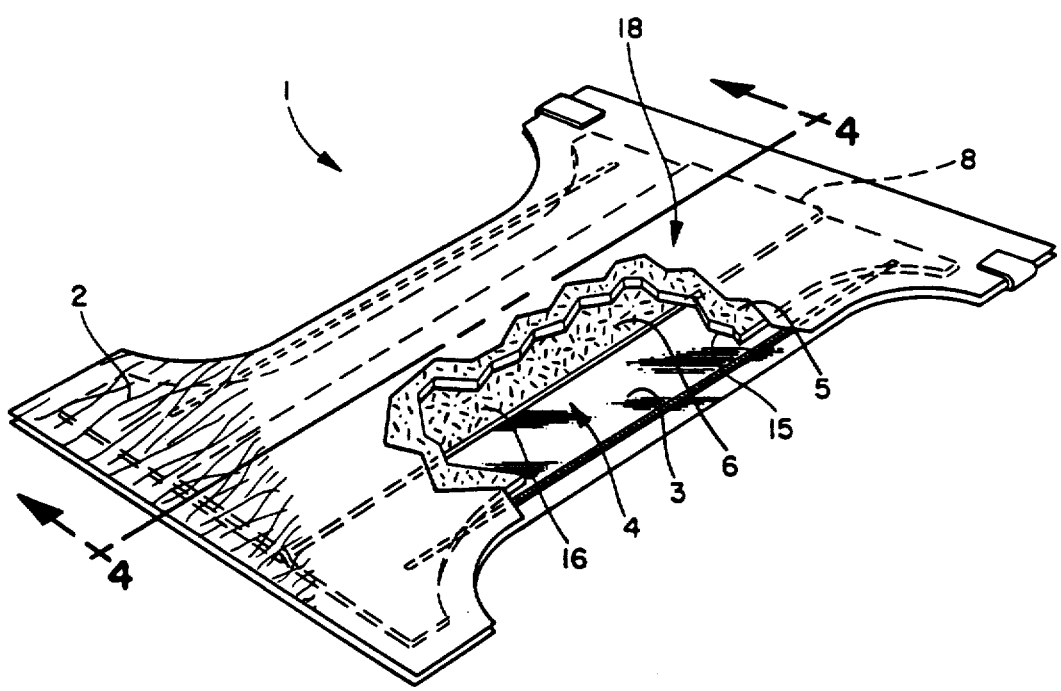
FIG. 3 is a perspective plan view of a second preferred embodiment of the invention, without the superabsorbent included therein.
Figure 4:
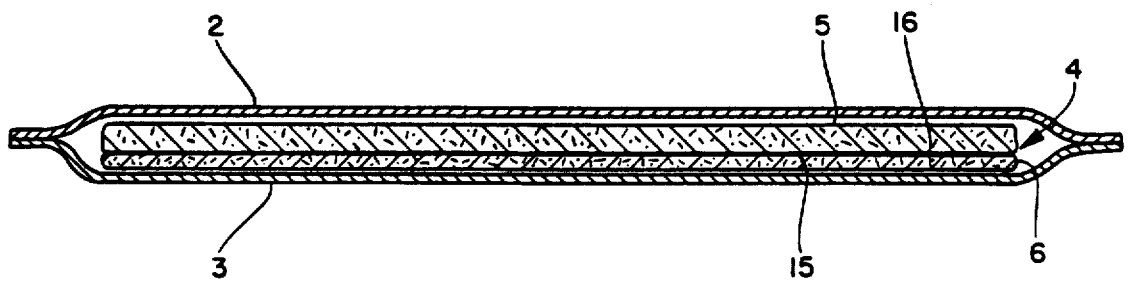
FIG. 4 is a longitudinal cross-sectional view taken along line 4—4 of FIG. 3.
Figure 5:
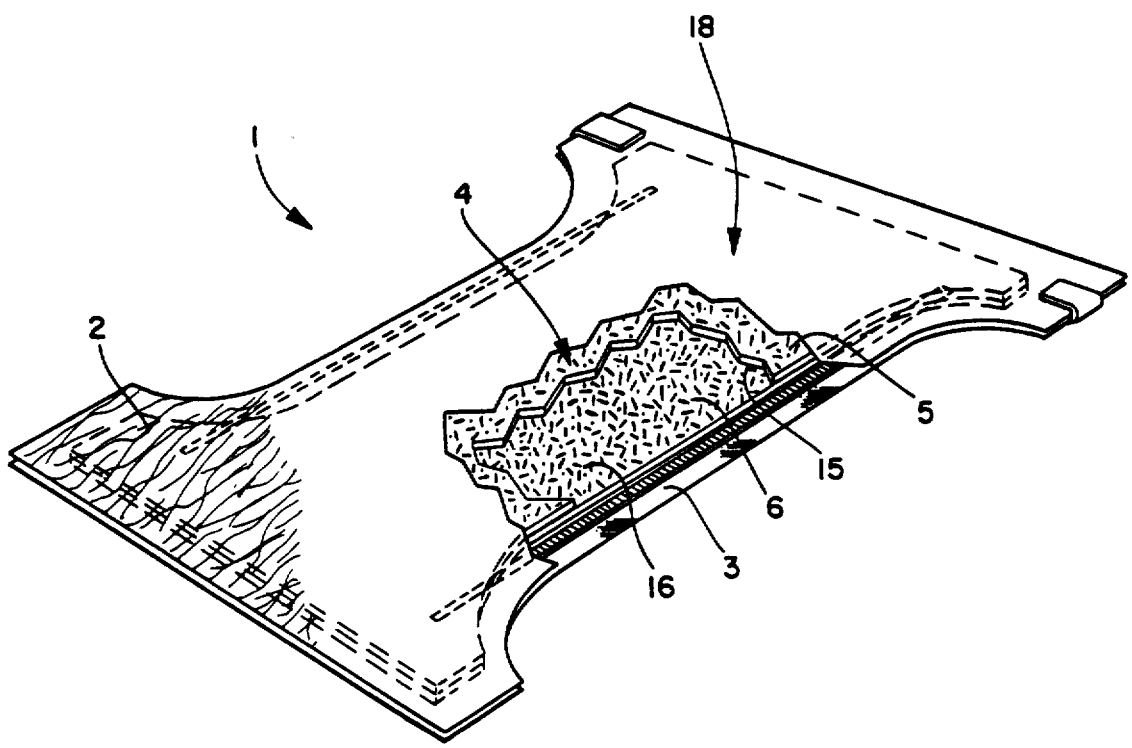
FIG. 5 is a perspective plan view with several cutaway portions of a third preferred embodiment of the present invention without the superabsorbent material included therein.

Alternative embodiments according to this aspect of the invention are shown in FIGS. 3 through 5. According to the second preferred embodiment in FIGS. 3 and 4, the higher density layer 6 extends as a strip along the entire length of the diaper. According to the third preferred embodiment shown in FIG. 5, the higher density layer 6 is coextensive with the entire lower density layer 5.

Yet another alternative to each of the embodiments described above is that of varying the pore size without necessarily varying the density. For example, the present inventor has discovered that the fine fiber dimensions of hardwood fluff can be utilized to advantage by substituting at least about 50%, and preferably about 80% to 100%, hardwood fluff fibers of approximately the same density as the lower density softwood fluff fiber layer 5 for the higher density softwood fluff fiber layer 6. This can be done because the hardwood fluff has a smaller pore size than the softwood fluff material. As a result, if hardwood fluff fibers are used as a replacement for the higher density softwood fluff fibers, two different pore size distributions will still be obtained within the scope of the invention, even if the density of each layer is the same. Thus, for example, a two component fluff sandwich comprising a coarse pore structure in the upper layer 5 obtained from a predominately softwood fluff pulp and a fine pore structure in the lower layer 6 comprised of a preponderantly hardwood fluff pulp fluff, densified throughout to one density (preferably approximately 0.1 g/cm$^3$) can successfully be used with similar results to those obtained according to the embodiments described.

The second aspect of the invention relates to including a portion of superabsorbent material (SAM) 9 as part of the liquid absorbing material 4. The term "superabsorbent material" as used herein refers to one or more hydrocolloid materials capable of absorbing many times its own weight of water or aqueous fluid. These materials are generally prepared by polymerizing one or more monomers which, if homopolymerized by conventional methods, would form water soluble polymers To render them water-insoluble and suitable for the present invention, these polymers or mixture of polymers are typically reacted, frequently with a crosslinking agent, to form crosslinked polymers, thereby introducing a limited water-insolubility while retaining susceptibility to swelling in water and water-containing fluids. Pseudocrosslinking may also be achieved by chain entanglement of high-molecular weight polymers, thus effecting water insolubility (see, e.g., U.S. Pat. No. 4,340,706). Typically, these hydrocolloids are salts of polyacrylic acid and variations thereof, such as methacrylic acid. Commercially, they are available under the trademarks WATER LOCK J-500 from Grain Processing Co.; ABASORB 720 from Arakawa Chemical, (U.S.) Inc.; and Aqualic-CA from Mitsui Co. Alternative superabsorbents also may include hydrophilic polymer grafts onto starch or cellulose backbones and crosslinked carboxylated celluloses.

Figure 6:
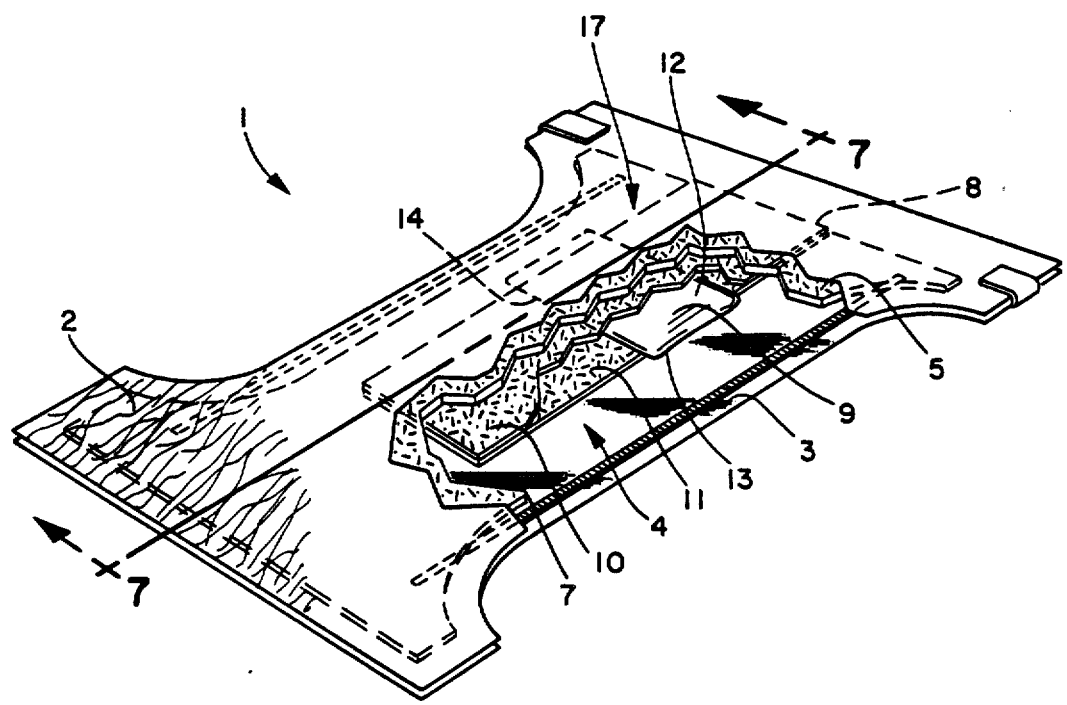
FIG. 6 is a perspective plan view of a fourth preferred embodiment of the present invention, including a portion of superabsorbent material incorporated therein.
Figure 7:
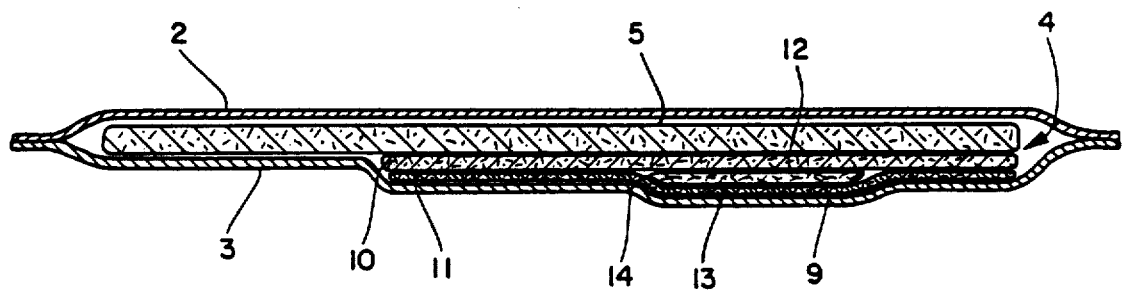
FIG. 7 is a longitudinal cross-sectional view taken along line 7—7 of FIG. 6.

In FIGS. 6 and 7 the fourth preferred embodiment is shown wherein the superabsorbent material 9 is sandwiched between a first higher density component 10 and a second higher density component 11. These first and second higher density components 10, 11 are disposed in an equivalent position to the higher density layer 6 in the first three embodiments discussed above. However, it is generally preferred that the superabsorbent material 9 is localized in an area 17 slightly above a region midway between the target area 7 and the upper edge 8. Thus, the superabsorbent material 9 provides an additional reservoir for liquid waste that has been drawn up the diaper by the higher density layer 6.

An important advantage of this aspect of the invention is that it assists in fluid distribution along the length of the superabsorbent material. Generally, superabsorbents 9 disposed in a fiber matrix enhance fluid distribution in the direction corresponding to the thickness of the liquid absorbing material 4. However, due to the swelling nature of the superabsorbent material 9, wicking in the plane of the fiber matrix bearing the superabsorbent 9 is severely hindered. According to this aspect of the present invention, wicking across the entire length of the superabsorbent material 9 is accomplished by sandwiching the superabsorbent material 9 between the first high density component 10 and the second high density component 11. Thus, the liquid waste is brought into contact across an upper surface 12 and a lower surface 13 of the superabsorbent material 9 rather than across a bottom edge 14 thereof. This is an improvement over border-to-border transfer of liquid waste, in much the same way as the first aspect of the invention, described in connection with FIGS. 1-5, provides the improvement of surface to surface contact between the lower density layer 5 and the higher density layer 6.

Figure 8:
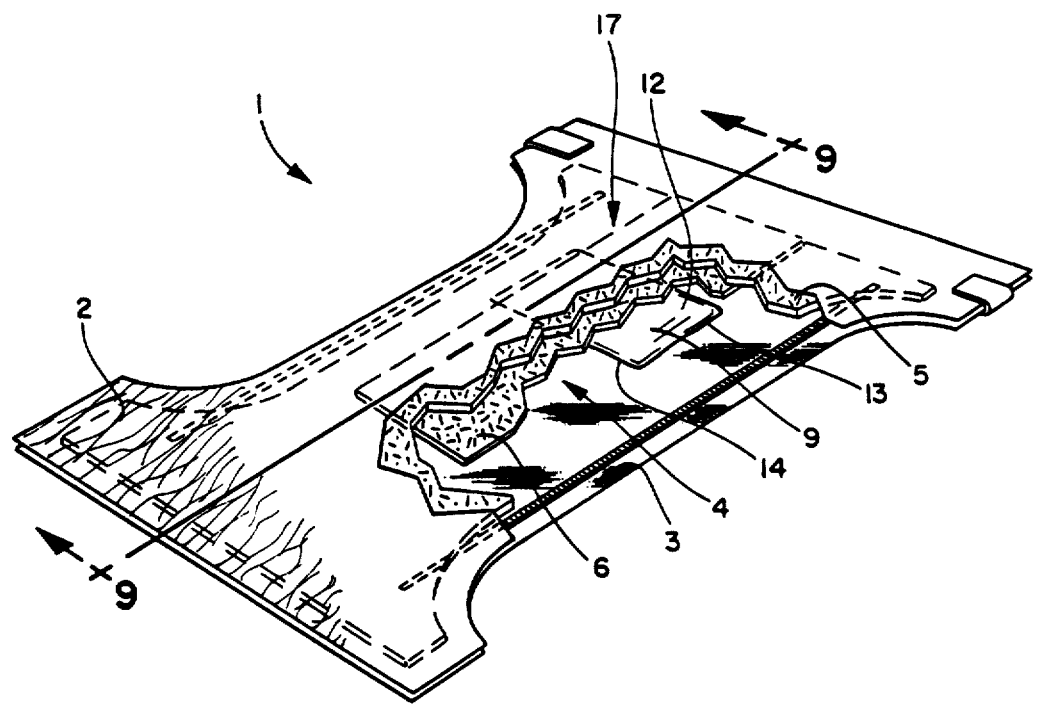
FIG. 8 is a perspective plan view of a fifth preferred embodiment of the present invention including a portion of superabsorbent material incorporated therein.
Figure 9:
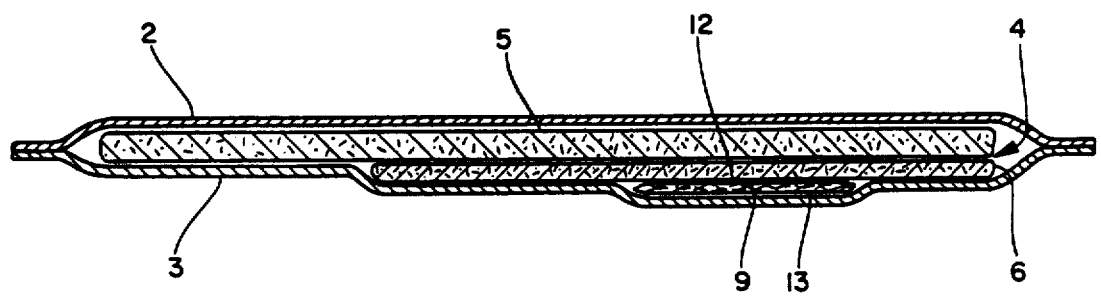
FIG. 9 is a longitudinal cross-sectional view taken along line 9—9 of FIG. 8.
Figure 10:
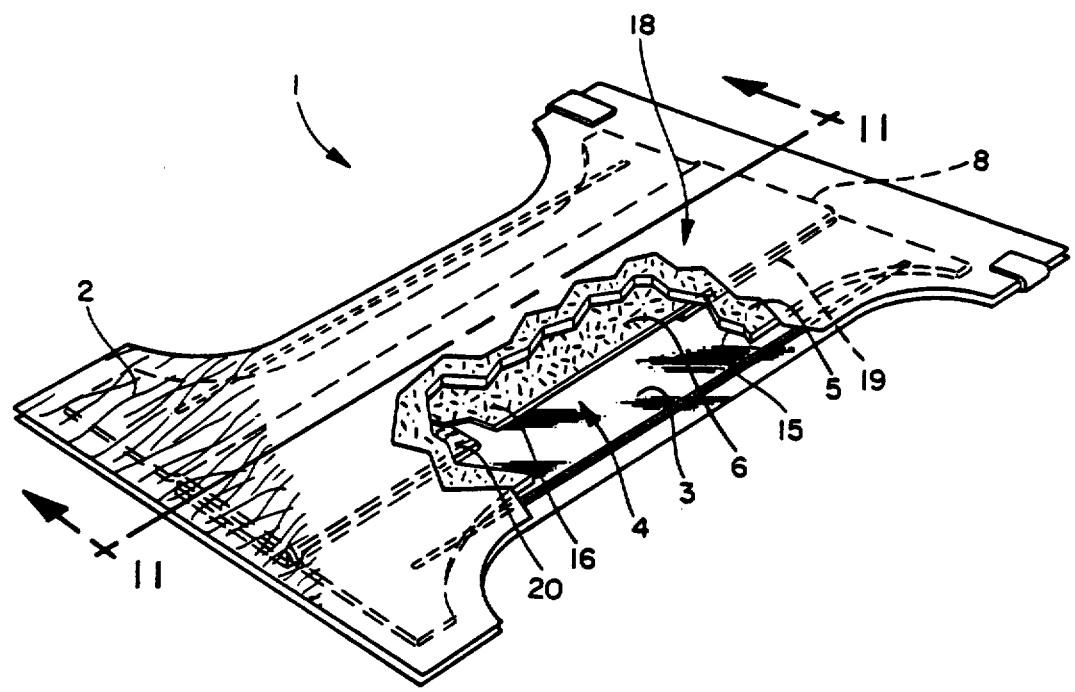
FIG. 10 is a perspective plan view of a sixth preferred embodiment of the invention wherein the superabsorbent material is disposed in a pair of spaced fluid retention pouches.
Figure 11:
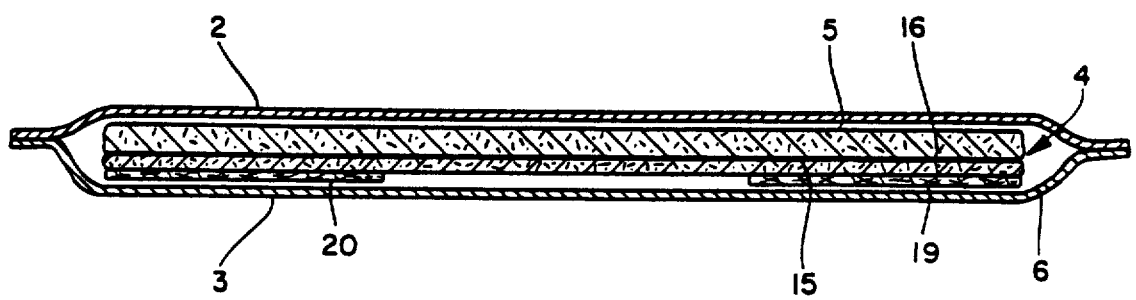
FIG. 11 is a longitudinal cross-sectional view taken along line 11—11 of FIG. 10.

FIGS. 8 and 9 show an alternative embodiment wherein the superabsorbent material 9 is disposed adjacent the outer, liquid impermeable cover 3, and then covered with the single higher density layer 6 which is in turn covered with the lower density layer 5.

Of course, still further alternative embodiments are provided by using a softwood fluff pulp in the layer 5 and a hardwood fluff pulp in the layers 6 (FIGS. 8 and 9), or 10 and 11 (FIGS. 6 and 7), with uniform densification of all layers to about 0.1 g/cm$^3$, or in the range of about 0.1 g/cm$^3$ to about 0.15 g/cm$^3$. Yet further variations within the scope of this invention include using a softwood fluff pulp of a first density in combination with a hard wood fluff pulp of a second density, wherein the second density is preferably higher than the first density.

The term "density" as used herein refers to the density of the composite structure of the lower density layer 5 or the higher density layer 6, and not the actual fiber density. (The actual fiber density is about 1.5 g/cm$^3$.) The density of the lower density layer 5 should be in the range of about 0.03 to about 0.14 g/cm$^3$, with the preferred range, in light of considerations of integrity and bulk, at about 0.07 to about 0.11 g/cm$^3$. The higher density layer 6 should have a density in the range of about 0.14 to about 0.3 g/cm$^3$, and preferably in the range of about 0.16 to about 0.22 g/cm$^3$ for providing the desired capillarity without excessive stiffness. The density for these preferred ranges is a density measured under a load of 0.2 psi. An important consideration in selecting suitable ranges for the higher density fluff and lower density fluff is that although there should be two distinct pore size distributions, one for each of the respective layers of fluff, these pore size distributions should overlap because this will permit flowback from the high density layer back to the low density layer.

The densified layer 6 may be a multiple ply layer rather than merely a single ply layer, and the ply may increase in density across the width or length of the layer 6 within the specified range or can be of uniform density. The basis weight of the lower density layer 5 should be in the range of about 150 to about 500 g/m$^2$ to provide the desired aesthetic appearance and comfort of the diaper. The basis weight of the higher density layer 6 should be in the range of about 150 to 1250 g/m$^2$.

It is preferred that the higher density layer 6 be substantially separately rather than integrally formed with the lower density layer 5, to achieve better moisture distribution therethrough. It should be noted, however, that the layers 5 and 6 are "substantially separately" formed even when formed in the same machine, one on top of the other, with some admixing at the interface. By the "substantial separate" terminology, it is intended only that two substantially discrete layers are formed, rather than a substantially single layer having a "skinned" surface, such as described in U.S. Pat. Nos. 2,952,260, 2,955,641, 3,017,304, 3,060,936, and 3,494,362 to Burgeni. Thus, densification should be achieved uniformly through the higher density layer 6, and care should be taken to avoid substantial skinning, where such skinning is as described in the Burgeni patents or in the Aberson U.S. Pat. No. 4,103,062. Skinning produces undue stiffness in the fluff and results in low absorbent capacity in the bonded (skinned) layer. Skinning can be prevented by avoiding excess moisture and by maintaining both platens at approximately the same temperature to avoid condensation through the thickness of the material. The present invention avoids the densification of the fluff to the point of forming a skin layer so that the densified fluff layer 6 retains at least about 80% void volume, resulting in significant absorbent capacity.

The layer 6 is densified in a heated press, such as can be obtained by Dake, Grand Haven, Michigan, as a "Dake Laboratory Press", Model No. 44-148 which includes heated platen operated under suitable conditions of temperature and pressure as known in the art to achieve the desired density. Alternatively, a heated calender nip is suitable for use in the densification process, as known in the art.

Comminuted wood pulp (fluff) is preferred for this invention, but other cellulose fibers such as cotton linters can be used. The preferred fluff is southern pine kraft wood pulp (i.e., made according to the sulfate process commonly known in the art) which has been bleached, such as can be purchased from ITT Rayoneer or International Paper Company. A suitable hardwood fluff pulp is southern hardwood kraft obtainable from Weyerhauser as "New Bern 309".

The superabsorbent material can be obtained from the Grain Processing Company of Muscatine, Iowa as their product Water Lock ™ J-500 or A-100. Suitable inner liners 2 and outer covers 3 are easily obtained and well known in the art.

Combined with these alternative absorbents is a soft, compressible fluid transfer portion or layer comprised of synthetic fibers such as polyester/polypropylene. This transfer layer is integrally bonded to a top liner at spaced apart sites to provide densified zones for fluid transfer. Such a web is described in U.S. Pat. No. 4,397,644. The top liner is a pattern bonded spunbonded web also of synthetic fibers such as polypropylene, polyester and the like. The combined basis weight of the liner/transfer layer should be in the range of about 30–40 g/m² preferably 30–100 g/m² with the liner being about 10–15 g/m² and the transfer layer about 20–90 g/m². The combined liner/transfer layer has a thickness o 0.1 to about 1.0 cm. It must have a wetting finish throughout.

The transfer layer is typically a carded web of polyester polyolefin fiber containing from 0 to 100% weight polyester fiber, preferably 25–50% weight polyester staple having a thickness of from about 3–6 denier, a length of about 1–2 inches and containing sufficient surfactant finish to be wettable. Two-inch polyester staple, Type T808, a hollow fiber, at 5.5 denier from E. I. duPont Co. with a wettable finish is preferred although other wettable polyester staple fibers would work. Suitable polyolefin fibers have a thickness of from about 3–6 denier Polypropylene Type T-123 from Hercules Inc. has a wettable finish with the 3-denier, 1⅞ inch staple preferred. The web is only bonded together through the spaced apart bonds which attached it to the top liner, which are typically achieved through thermal or ultrasonic bonding.

The layer may also be formed by other nonwoven processes such as spunbonding wherein the filaments are spun and collected on a wire screen without bonding and then bonded to the prebonded liner as described above. It must have a wetting finish as is achieved by treating with 0.2–0.5% Triton X-102 from Rohm and Haas Co.

Of course, many changes and modifications can be made to the preferred embodiments described herein without departing from the spirit of the invention. For example, the densified fluff layer 6 could also be used with other absorbents such as coformed (meltblown polymer fibers combined with wood pulp and/or staple fibers) webs, carded webs, air-formed (staple wood pulp blends) webs and the like, at a lower density. Further, the absorbent structures described herein have applications to embodiments other than diapers, such as to sanitary napkins or other hygienic media. Therefore, it is intended that the preferred embodiments described in this specification be regarded as illustrative rather than limiting and it is intended that the claims, including all equivalents, define the scope of the invention.

The advantages resulting from this invention will be clearly understood with respect to the following examples and test data.

EXAMPLE I

The high density fluff was prepared by running the fluff into a hot calender nip (steel on hard rubber) at 250° F. at a speed of 10 ft/min. The nip pressure was sufficient to give a measured density on standing overnight of 0.15 g/cm³. Alternatively the fluff could have been pressed in a blotter lined platen press heated to about 250° F. for about 5 seconds, with sufficient pressure to achieve the desired fluff density.

The lower density fluff was prepared by passing it through a calender nip at 250° F. at a speed of 10 ft/min and sufficient pressure to achieve a measured density on standing overnight of 0.1 g/cm³.

In both cases the fluff was prepared from southern pine bleached kraft wood pulp, and was cut to dimensions such that the weight conditions set forth in Table I below were met. The combined low density fluff and high density fluff weight are given in the first column of Table I. The total absorbent weight was maintained at about 37 grams for each diaper, except for the one containing superabsorbent. The diaper with superabsorbent located as shown in FIG. 8 contained an additional 7 grams of superabsorbent composite consisting of about 3 grams of particulate superabsorbent (Water Lock ™ A-100 from Grain Processing Co., Muscatine, Iowa); about 3 grams of polyolefin; and about 1 gram of porous nonwoven wrap. The composite was made in accordance with the teaching of Mazurak and Fries, as set forth in U.S. Pat. No. 4,381,782. The diaper construction was completed by sandwiching the absorbent composite between a porous spunbonded polypropylene liner (23 g/yd²) and a polyethylene film outer cover, sealed together with adhesive at the diaper perimeter. Five types of diapers were constructed in this fashion, corresponding to the diaper description of Table I.

Each of the diapers was then subjected to a 15 minute vertical wicking test with synthetic urine, followed by 15 minutes of equilibration out of contact with the urine bath. The results of this testing are shown in Table I and FIGS. 14–18.

In this test the preweighed diapers were mounted on a lucite plate (⅛"×13"×14") with the impervious poly backing adjacent the plate surface. The diaper was symmetrically wrapped around the edge of the plate with the longitudinal dimension of the diaper parallel to the long dimension of the plate. The waist line edges of the diaper were mounted on the plate with masking tape, the elastic leg bands being cut in 2 or 3 places to facilitate the mounting.

The plate was suspended vertically over a fluid bath contained in a glass tray with the longitudinal dimension of the diaper perpendicular to the fluid surface. The fluid was then brought into contact with the lower edge of the diaper so that the diaper edge was slightly immersed, and was maintained in this position for 15 minutes. The diaper was then removed from fluid contact and allowed to hang in the same vertical orientation for 15 minutes equilibration. The fluid used for the diapers in Table I was a synthetic urine composed of by weight 1% urea, 0.01% Pluronic 10R8 surfactant to bring the surface tension to about 56 dynes/cm, and 0.04% sodium azide preservative.

After equiliberation the diapers were removed from the plate and weighed and the fluid pick up noted. The results are summarized in Table I and represent the average of seven measurements on each diaper design.

After weighing, the diapers were laid horizontally on a 3"×15" cutting die which was segmented into 9, 1.7-inch zones with cutting edges across the die width as well as the outer perimeter. Several quick blows with a wooden mallet divided the 3-inch wide absorbent strip along the longitudinal axis of the diaper into 9 segments. The absorbent component in each segment was weighed, oven dried and reweighed and the fluid pick up determined on a gram per gram or fiber basis (corrected for deposited solids from the fluid).

In the case of the diaper with the superabsorbent pouch, the synthetic urine composition was adjusted to more closely simulate the electrolyte composition of baby urine, namely: 0.31 g. $CaH_4(PO_4)_2 \cdot H_2O$, 0.68 g. $KH_2PO_4$, 0.48 g. $MgSO_4 \cdot 7H_2O$, 1.33 g. $K_2SO_4$, 1.24 g. $Na_3PO_4 \cdot 12H_2O$, 4.4 g. NaCl, 3.16 g.KCl, 0.4 g. $NaN_3$, 8.56 urea and 0.1 g. Pluronic 10R8 per liter, using distilled water as the solvent. The components were added to 900 mls of distilled water in the order given and each dissolved before the next component was added, and finally diluted to 1 liter.

Figure 14:
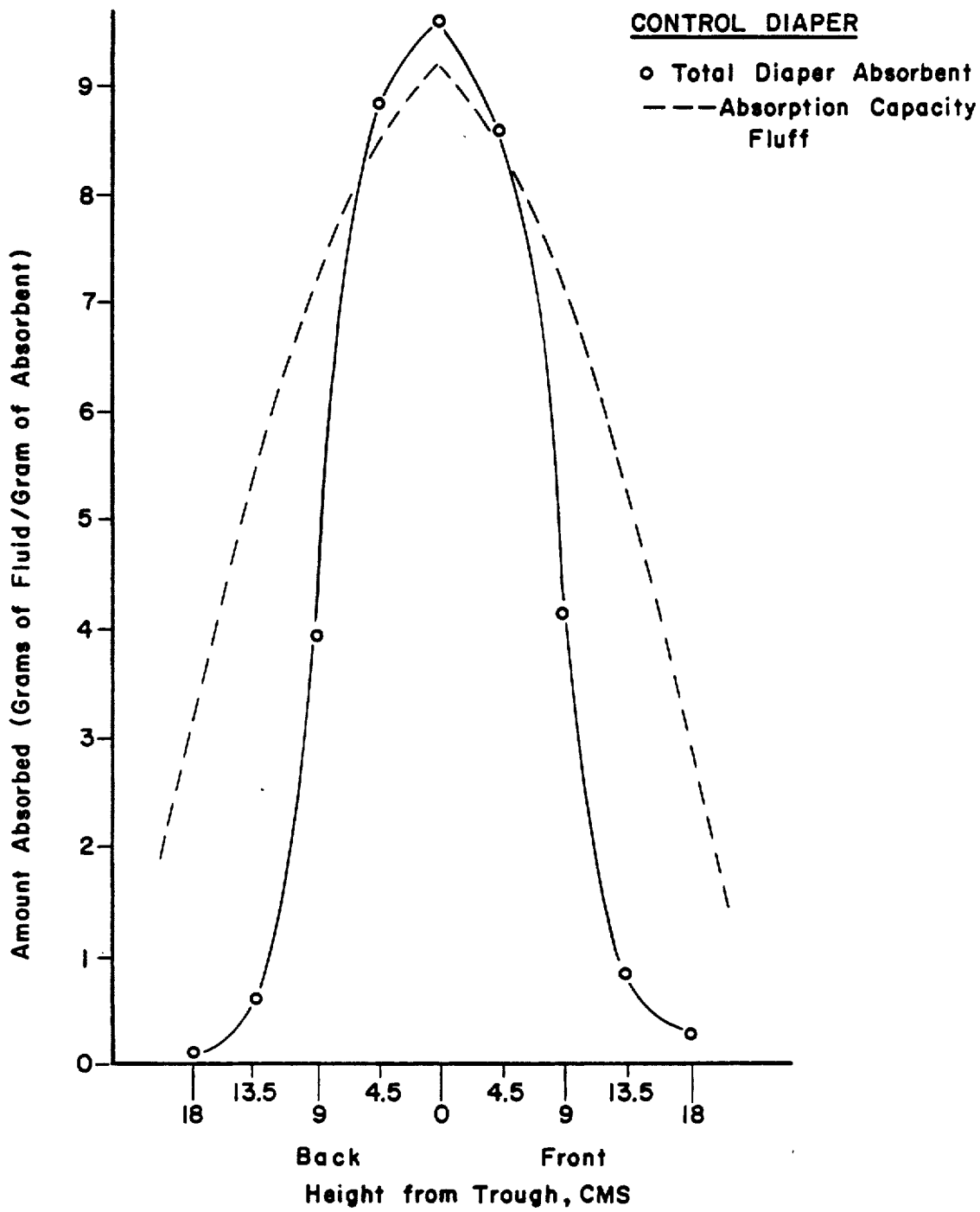
FIG. 14 is an absorbency profile for the control diaper tested in Example 1.

The dotted curve in FIG. 14 represents the equilibrium capacity for the low density fluff at the indicated hydrostatic tensions as measured in a capillary tension cell. It is apparent that only at short wicking distances (4.5 cm) does the fluff reach its ultimate capacity. At the greater wicking heights (9-18 cms) it is well below its capacity.

Figure 15:
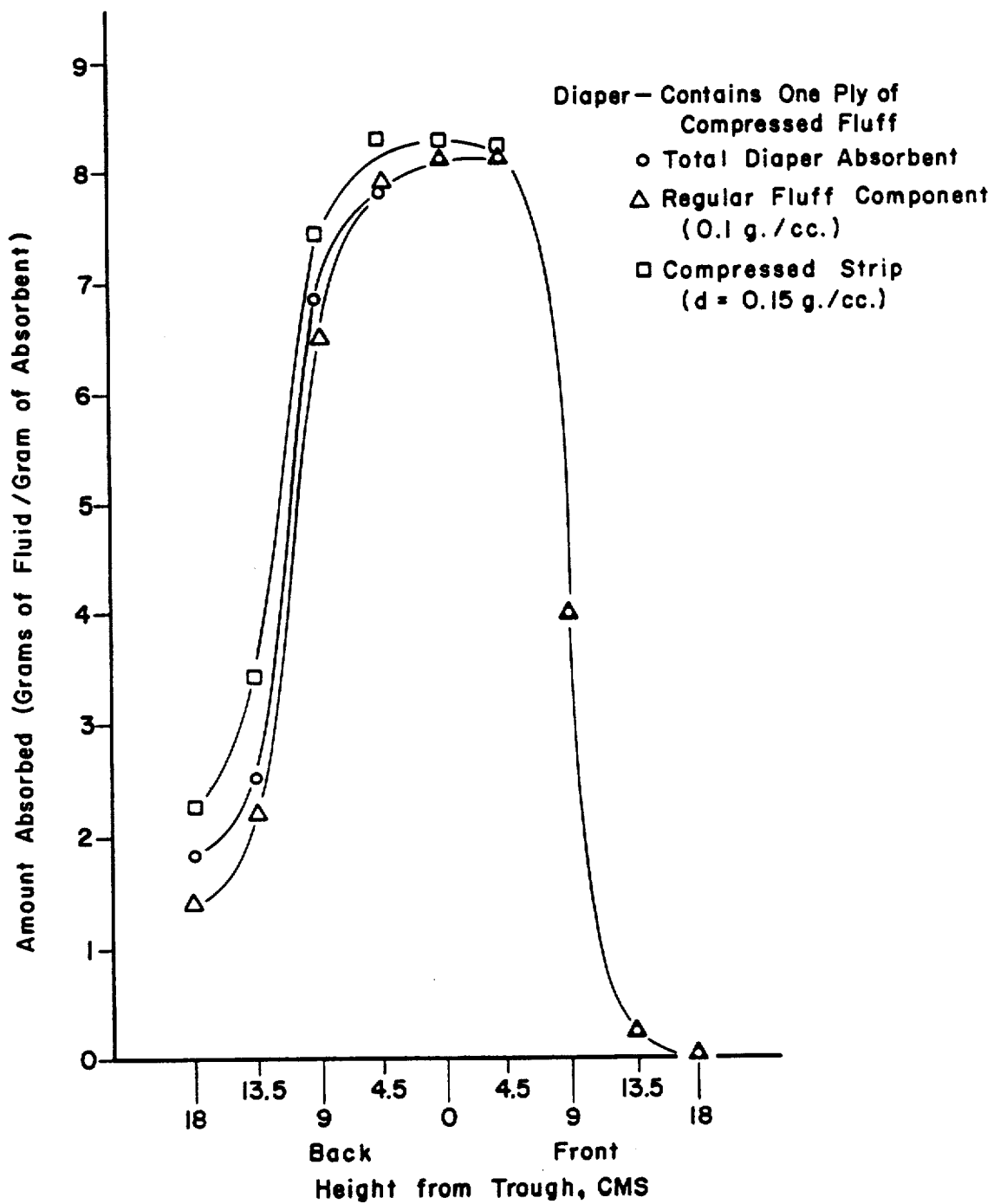
FIG. 15 is an absorbency profile for the diaper containing one ply of compressed fluff in addition to the regular fluff component as discussed in Example 1.
Figure 16:
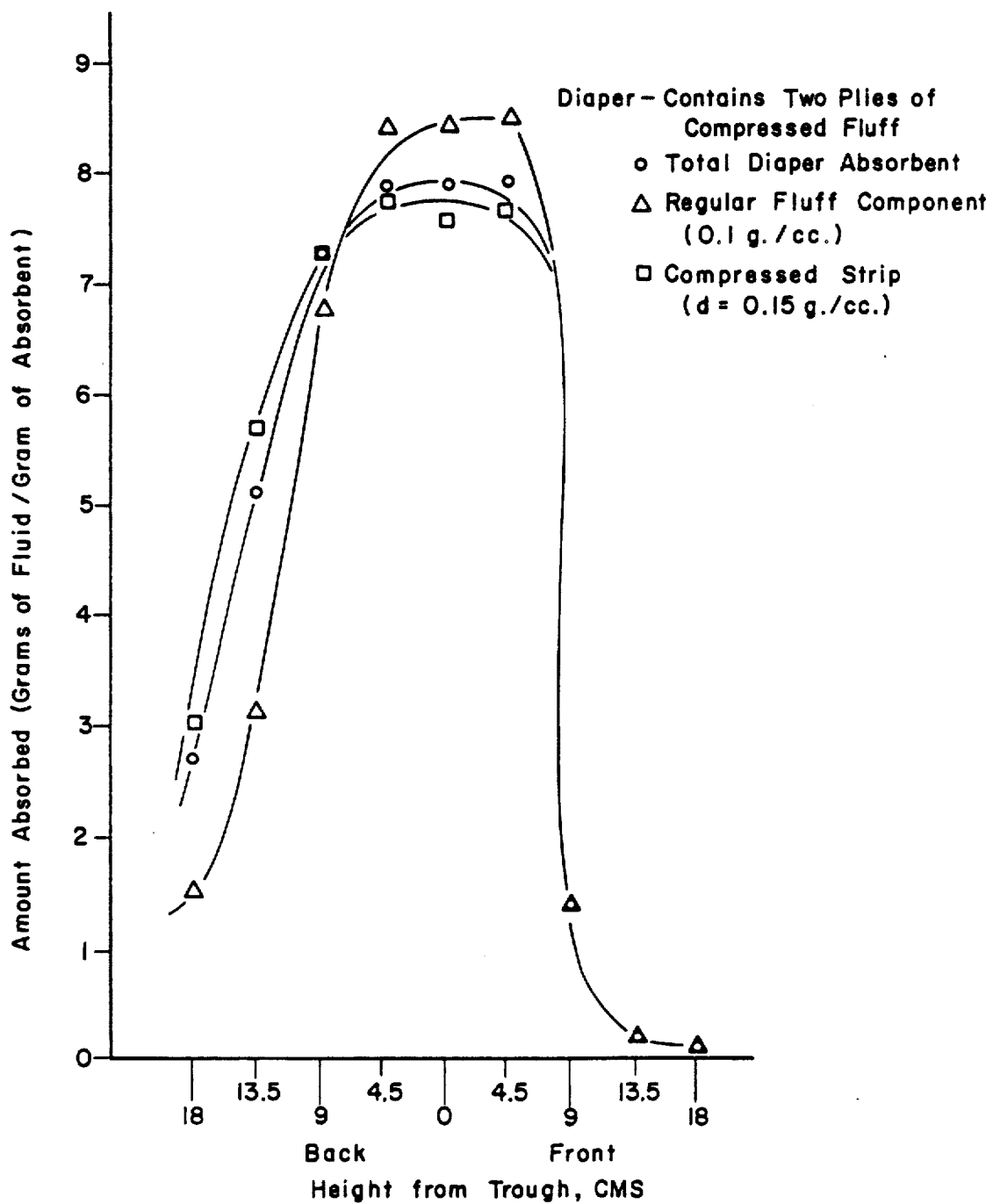
FIG. 16 is an absorbency profile for the diaper containing two plies of compressed fluff in addition to the regular fluff component as discussed in Example 1.
Figure 17:
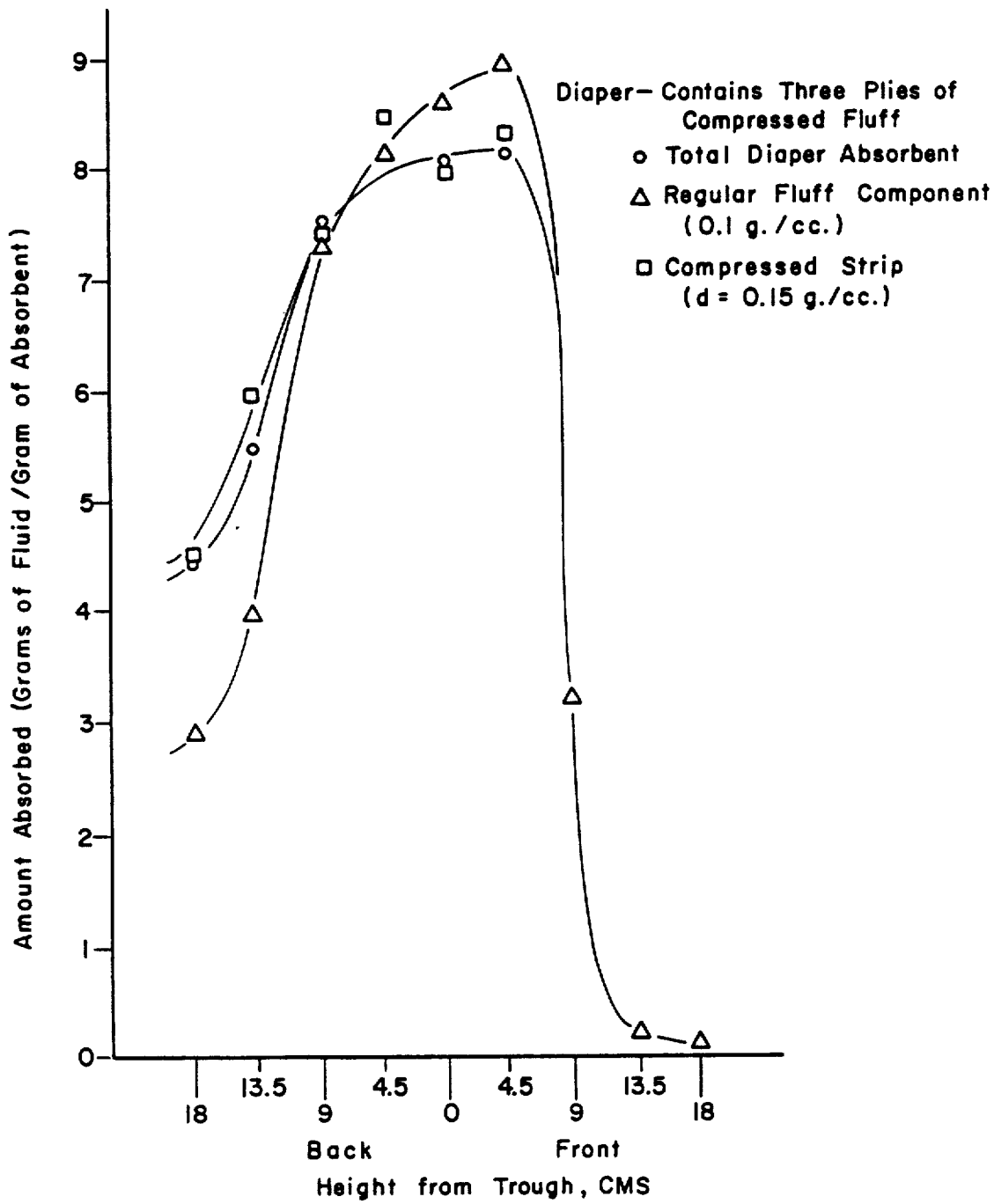
FIG. 17 is the absorbency profile for the diaper containing three plies of compressed fluff in addition to the regular fluff component as described in Example 1.

FIGS. 15-17 demonstrate the ability of the densified fluff layer to pull the fluid up against the hydrostatic heads indicated. Comparison of the fluid level in the low density fluff in the back of the diaper with that in the same material in front at the corresponding head is a measure of the effectiveness of the high density fluff to improve the utilization of the low density material (e.g. 2.8 g/g back vs. 0.1 g/g front at 18 cms head, FIG. 17).

Figure 18:
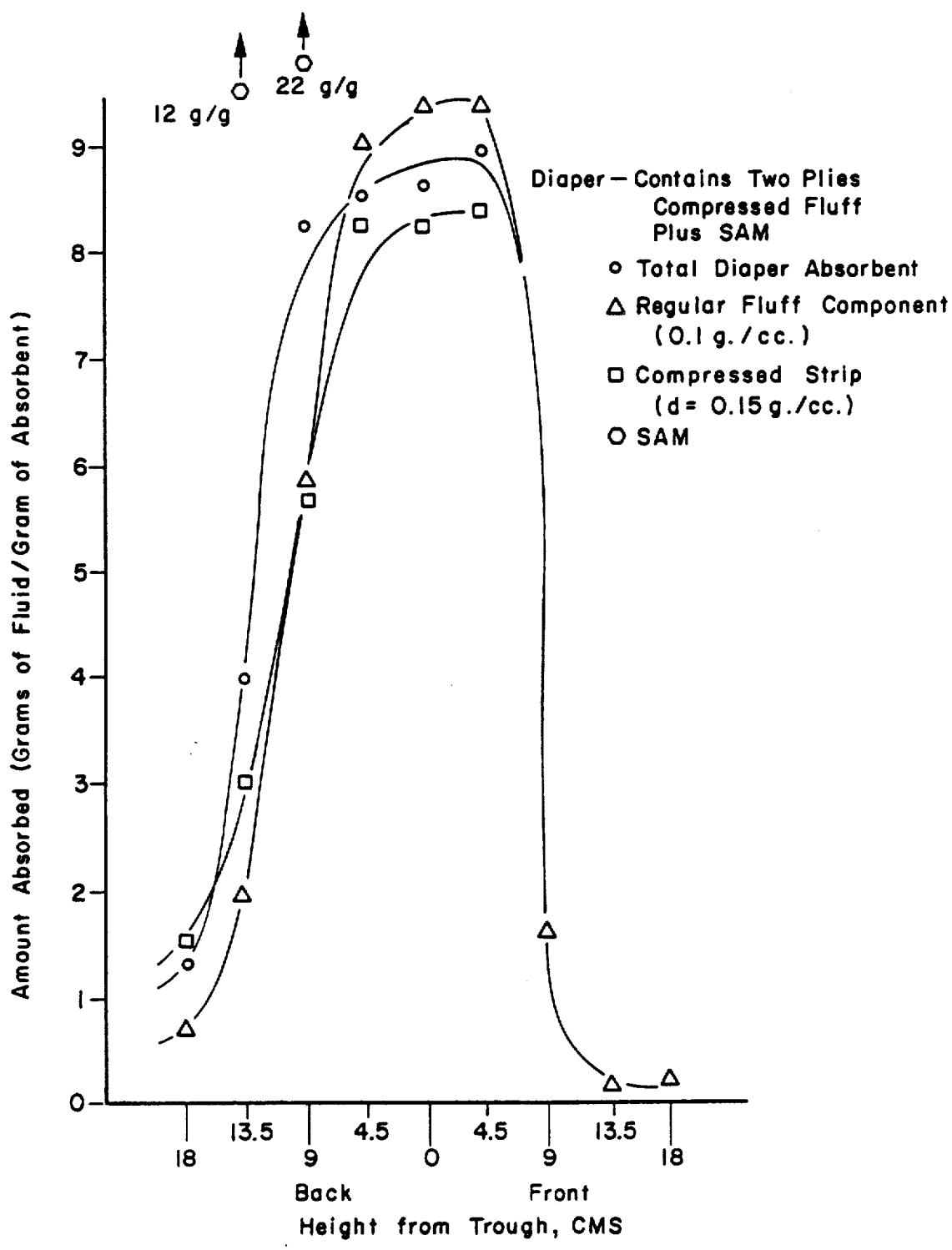
FIG. 18 is the absorbency profile for the diaper containing two plies of compressed fluff plus a portion of superabsorbent material as described in Example 1.

FIG. 18 shows the effectiveness of the densified layers in carrying and transferring fluid to the superabsorbent. The levels of fluid pickup in the superabsorbents are 12 and 22 g/g respectively at the 9 and 13.5 cm heads. Comparing this to FIG. 16 illustrates the effectiveness of the superabsorbent in diverting fluid from the fluff components at the highest heads.

It is apparent from these results that fluid distribution is greatly enhanced up the back of the diaper in the designs with densified fluff layers. The contrast with the fluid distribution in the front of the diaper, where densified fluff layer is absent, is very evident from the figures.

Of course, better fluid distribution in the front as well as the back of the diapers would be obtained when the second and third preferred embodiments are followed. However, the first preferred embodiment was followed for the purposes of these tests because the diaper front tends to become fairly thoroughly wetted when the release of waste fluid occurs when the child wearing the diaper is lying on its stomach, for example when it is sleeping.

Moreover, the results demonstrate that the fluid distribution in the low density fluff areas is significant. This demonstrates the unexpected synergism obtainable in these designs In the instance of the superabsorbent diaper, which was made in accordance with the fourth embodiment set forth in this specification, the superabsorbent material drained substantial fluid from the higher regions of the diaper However, these regions toward the upper edge 8 of the diaper provide surplus absorbing capacity if needed.

TABLE I

| | Whole Diaper Vertical Wicking Test* | | | |
|---|---|---|---|---|
| Diaper Description | Absorbent Weight g. | Weight of Comp. Fluff g. | Amt. of Fluid Absorbed g. | Fluid Absorbed Over Control % |
| Control Diaper | 36 | 0 | 140 | — |
| Diaper containing 1 ply of compressed fluff | 38 | 7 | 171 | 22 |
| Diaper with 2 plies of compressed fluff | 37 | 14 | 191 | 37 |
| Diaper with 3 plies of compressed fluff | 35 | 21 | 203 | 45 |
| Diaper with 2 plies of compressed fluff & SAM | 43** | 14 | 215 | 54 |

*Absorption time: 15 minutes followed by 15 minutes equilibration time.
**Contains 7 g. of assembly containing 3 g. SAM.

EXAMPLE II

The present inventor has discovered that similar functionality to the higher density fluff can be achieved with finer fiber, hardwood pulp fluff but at normal density (0.1 g/cm³). This discovery was made following the observation of a remarkable similarity in the pore volume distribution of 0.1 g/cm³ density hardwood fluff and that of 0.2 g/cm³ softwood fluff. The following tables compare the vertical wicking properties of softwood and hardwood fluff.

The vertical wicking test was somewhat similar to that conducted with whole diapers described above. This test was conducted on 3"×15" strips of the absorbent material mounted on a ⅜"×5"×14" lucite plate in the same orientation and manner described for the diapers. A nylon mesh screen was used to support the fluff strip on the lucite (acrylic) plate. The plate and strip were then suspended from weight-sensing means such as a load cell in an Instron tensile tester. The synthetic urine (in these cases the second or salt-containing formulation) was then put in contact with the lower edge of the absorbent strip and the amount of fluid absorbed as a function of time is recorded at several time intervals for the 15 minute duration of the test. The amount absorbed was calculated as the grams per unit basis weight of 1 gm/cm² per unit width (1 inch). The vertical wicking capacity is defined as the amount absorbed in the defined units at the end of the 15 minute test. The reported rate was that measured from the plot of amount absorbed/unit basis weight/unit width versus time½ over the time interval of 7-21 seconds. The test was replicated six times and the results reported are averages of these six measurements.

Fluid distribution in this test was measured by die cutting the sample immediately following the completion of the test, the same manner described for the whole diapers. In this case zones corresponding to the same vertical heights were combined to give the results shown in Table III.

As may be concluded from the results in Table II, the vertical wicking capacity of 0.1 g/cm³ density hardwood fluff corresponds closely with that of 0.2 g/cm³ density softwood fluff. The initial wicking rate of the hardwood fluff falls between the two softwood fluffs. The fluid distribution pattern in Table 111 also shows the similarity of the hardwood fluff and the 0.2 g/cm³ density softwood fluff. These results imply a slightly larger average pore size for the former than the latter.

Hence, a combination of softwood and hardwood fluff at 0.1 g/cm³ density should have similar fluid distribution properties to a two-density sandwich of softwood fluff, as previously described in this disclosure.

TABLE II

VERTICAL WICKING CAPACITY/RATE
(Showing similarity in capillarity of softwood kraft at 0.2 g/cm³ and hardwood kraft at 0.1 g/cm³ density)

| Material | Density (g/cm³) | *Vertical Capacity G/UBW/UW | Wicking Rate G/UBW/ UW/SEC½ |
|---|---|---|---|
| Softwood Kraft Fluff | 0.1 | 499 | 48 |
| Softwood Kraft Fluff | 0.2 | 573 | 36 |
| Hardwood Kraft Fluff | 0.1 | 580 | 42 |

*Units are grams per unit basis weight (1 g/cm²) per unit width (1 inch).

TABLE III

FLUID DISTRIBUTION IN VERTICAL WICKING

| | **Specific Absorbency (g/g) at Following Tensions | | | | |
|---|---|---|---|---|---|
| | 0 cm | 4.5 cm | 9 cm | 13.5 cm | 18 cm |
| Softwood Kraft (0.1 g/cm³) | 9.0 | 9.0 | 6.4 | 3.0 | 0.7 |
| Softwood Kraft (0.2 g/cm³) | 6.0 | 6.1 | 5.8 | 5.0 | 4.7 |
| Hardwood Kraft (0.1 g/cm³) | 8.2 | 8.1 | 7.2 | 5.3 | 3.3 |

**Tensions are measured as vertical distance from fluid source.

EXAMPLE III

This example is directed to a double fluff layer of softwood fluff over hardwood fluff. The hardwood fluff was a bleached kraft, South American Eucalyptus hardwood pulp. The two-ply fluff contained equal weights of the softwood and hardwood pulp layers. After densifying the layers to 0.1 g/cm³ density, the vertical wicking properties (same test procedure as for example 11) were as follows:

TABLE IV

VERTICAL WICKING PROPERTIES OF SOFTWOOD/HARDWOOD LAYERED BATT

| ***Vertical Capacity | ***Wicking Rate | ***Specific Absorbency At Following Tensions | | | | |
|---|---|---|---|---|---|---|
| | | 0 cm | 4.5 cm | 9 cm | 13.5 cm | 18 cm |
| 544 | 46 | 7.8 | 7.8 | 6.1 | 4.3 | 3.0 |

***Same units as in Tables II, III.

Comparing the distribution results for the double-layered fluff in Table IV with those for softwood kraft (Table III), it is apparent that the presence of the Eucalyptus layer greatly improves fluid wicking against the upper two hydrostatic heads (i.e. in the 13.5 cm and 18 cm zones). This is particularly impressive since the Eucalyptus only represents 50% of the two-ply structure.

EXAMPLE IV

A 40 g/m² web of meltblown polypropylene containing 40 percent by weight of superabsorbent (Waterlock J-500 from Grain Processing Company) was prepared. The superabsorbent was intermixed with the fine meltblown fibers (surface area about 1 m²/g) containing enough surfactant (e.g., about 0.3-0.5 percent Triton X-102 from Rohm & Haas Company) to assure wetting of the fiber matrix, the composite being densified to 0.1 g/cm³ during the manufacturing process.

When this web was subjected to the vertical wicking procedure described in Example II, the results presented in Table 5 were obtained. From these results it is apparent that the fluid wicks vertically 4.5 cms but then essentially stops, presumably because the swelling particles have restricted the fluid flow in the web by plugging the pores.

When this same web was placed beneath a softwood fluff layer, having a density of 0.2 g/cm³, in a diaper construction, and the whole diaper was subjected to the vertical wicking test (described in Example 1), the effect of the fluff layer as a fluid distributor for the superabsorbent was apparent. In Table 6, the fluid distribution is shown for the total absorbent composite, the fluff layer itself, and for the meltblown/ superabsorbent web.

Comparing the vertical distribution for the meltblown/superabsorbent web from the diaper (Table 6) with the data in Table 5, it is apparent that the densified fluff acts to wick the fluid higher and improves the distribution to the superabsorbent (compare at 9 cm height, 11.6 g/g vs. 1.1 g/g; and at 13.5 cm height, 2.7 g/g vs. 0.1 g/g). Note that both tests were similarly run for 15 minutes. Furthermore, if the tests were allowed to proceed further, the height wicked in the diaper would continue to increase, whereas wicking in the superabsorbent web alone would virtually stop.

Referring to FIGS. 10-13, it has further been found that, in addition to placement of superabsorbent material in a hydrophilic web, either of meltblown fibers or a composite nonwoven pouch 19, generally in the rear of the diaper, a similar pouch 19 containing the superabsorbent material can be disposed both in the front and the rear of the diaper.

It will be appreciated by those skilled in the art that the term "hydrophilic web", as used herein, is intended to encompass the superabsorbent-treated web of meltblown fibers (Example IV) to which surfactant has been added, making the composite web wettable, that is, the surfactant makes the normally hydrophobic surface of the fibers wettable by presenting a hydrophilic contact angle on the fibers. Hence, even though the fibers may not be hydrophilic as formed, the resultant web is wettable by addition of surfactant, allowing liquid distribution to the superabsorbent material contained in the web. Likewise, the pouch previously described, which is a web comprised of various materials randomly formed into a nonwoven matrix containing the superabsorbent material, may also be made hydrophilic by treatment with surfactant for purposes of aiding liquid distribution to the hydrogel.

The density of superabsorbent material may be graded either in the front or rear longitudinal direction, for example, by selective layering (not shown) of a plurality of superabsorbent-treated meltblown webs (each constructed in accordance with Example IV). By overlapping such a succession of webs so that the ends of the webs are spaced longitudinally from one another a successively greater composite web thickness, i.e., concentration of superabsorbent material, can be achieved as fluid progresses toward the end of the absorbent structure. Preferably, the superabsorbent material is not located in the crotch, providing better accumulation of liquid in the front and rear of the absorbent structure, the remaining portion of the urine not immediately absorbed and retained by the front fluid retention pouch 20 being absorbed through at least the first layer by the superabsorbent material located in the rear fluid retention pouch 19. Superabsorbent material which is located in the crotch tends to compete for liquid with superabsorbent material located remote therefrom in the front and rear of the absorbent structure, resulting in less urine distribution in remote areas of the absorbent structure and greater detrimental retention of urine in the central portion of the absorbent structure. Urine excreted in the "target zone" located in the front of the absorbent structure, of course, need not be further distributed to the rear end of the absorbent structure remote therefrom to be absorbed by the rear retention pouch 19. Preferably, the second layer 6 is employed to wick and distribute liquid to the rear of the absorbent structure for absorption and retention in the rear fluid retention pouch 19 as well as the upper absorbent layer 5, which layer 5 is thereby more fully utilized for liquid and stays drier to the extent fluid transported to the rear of the absorbent structure is retained in the rear pouch 19. The liquid distributed through the first layer may be absorbed and retained by the rear 19 as well as front 20 fluid retention pouches without using the second layer to wick liquid rearward, although the second layer is preferred for this purpose. Since the front pouch 20 is closest to the urine target zone, it reaches saturation capacity soonest. Fluid may bypass the front pouch 20, either before or after it is saturated, and be distributed either via the first layer 5 or, preferably, via the second layer 6, to the rear fluid retention pouch 19 for absorption and retention.

Remote storage of urine in the fluid retention pouches 19, 20 effectively locks the fluid away from the central crotch portion of the absorbent structure which does not contain superabsorbent material, which is advantageous because, among other reasons, the urine is kept away from mixing with fecal material, an alleged cause of diaper rash, and the urine is not allowed to pool in the crotch causing greater skin hydration of a wearer in the highly rash-prone perineal area of a wearer. In this regard, the second layer has been demonstrated herein as being particularly effective in wicking and distributing liquid to the rear portion of the absorbent structure where the liquid may then be transferred to the rear retention pouch or back into the hitherto underutilized rear end of the first layer due to the aforementioned overlap in pore size distributions.

Figure 12:
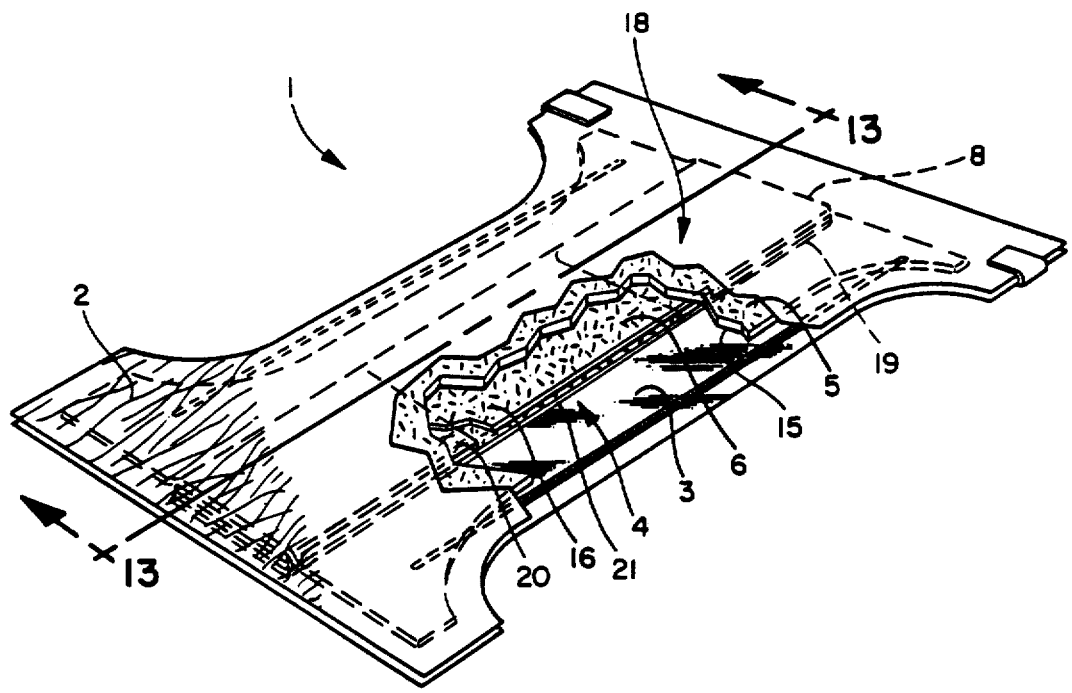
FIG. 12 is a perspective plan view of a seventh preferred embodiment of the present invention showing an alternative arrangement of the fluid retention pouches.
Figure 13:
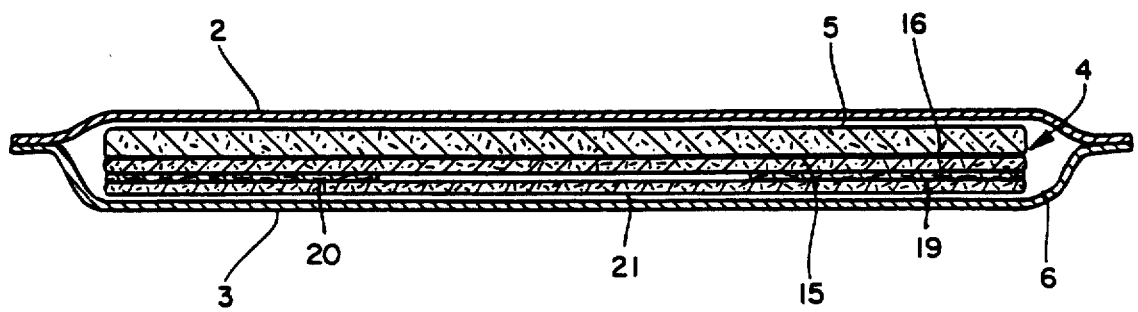
FIG. 13 is a longitudinal cross-sectional view taken along line 13 of FIG. 12.

An optional third layer 21, as shown in FIGS. 12 and 13 may be utilized to provide further wicking of fluid to the remote areas of the absorbent structure 4 away from the target zone.

In regard to flowback of the urine from the first layer toward the body, the composite liner described herein effectively restricts such flowback because the open porous structure of the composite liner effectively provides a comfortable, cushioned separation from the liquid present in the first layer while, in the first instance, providing a rapid drainage of excreted urine away from the body into the finer pore structure of the first layer, thence preferably into the still finer pore structure of the second layer by the suction activity of a capillary pore size gradient.

TABLE V

VERTICAL WICKING TEST MELTBLOWN/SUPERABSORBENT WEB

| Description | Basis Weight g/m² | Density g/cm³ | ***Specific Absorbency at Following Tensions* | | | | |
|---|---|---|---|---|---|---|---|
| | | | 0.0 cm | 4.5 cm | 9.0 cm | 13.5 cm | 18.0 cm |
| Meltblown Web with No Superabsorbent | 93 | 0.1 | 7.9 | 7.7 | 2.4 | 0.0 | 0.0 |
| Meltblown Web with 40% Superabsorbent | 139 | 0.1 | 23.0 | 20.5 | 1.1 | 0.1 | 0.0 |

*Hydrostatic Tension in cm. of water.
***Same units as in Tables II and III.

TABLE VI

VERTICAL WICKING TEST ON DIAPER CONTAINING MELTBLOWN/SUPERABSORBENT WEB

| Diaper Absorbent | Dry Absorbent Weight (g.) | Absorbent Component | ***Specific Absorbency at Following Tensions* | | | | |
|---|---|---|---|---|---|---|---|
| | | | 0.0 cm | 4.5 cm | 9.0 cm | 13.5 cm | 18.0 cm |
| Fluff densified to 0.2 g/cm³ over coextensive layer of Meltblown Web | 42.7 | Fluff | 7.5 | 7.2 | 4.5 | 2.5 | 1.5 |
| | | MB/SAM** | 18.8 | 19.7 | 11.6 | 2.7 | 1.0 |
| | | Combined Absorbent | 9.9 | 10.1 | 6.4 | 2.6 | 1.5 |

TABLE VI-continued
VERTICAL WICKING TEST ON DIAPER CONTAINING MELTBLOWN/SUPERABSORBENT WEB

| Diaper Absorbent | Dry Absorbent Weight (g.) | Absorbent Component | ***Specific Absorbency at Following Tensions* | | | | |
|---|---|---|---|---|---|---|---|
| | | | 0.0 cm | 4.5 cm | 9.0 cm | 13.5 cm | 18.0 cm |
| with 40% Superabsorbent (basis weight 139 g/m$^2$) | | | | | | | |

*Hydrostatic Tension, cms of water
**Meltblown Web/Superabsorbent
***Same units as in Tables II and III.

I claim:

1. In a disposable absorbent garment, an absorbent structure having opposed longitudinal ends, a central crotch portion and including a body-facing sheet, a backing sheet and liquid absorbing material therebetween, said liquid absorbing material comprising:

a first layer consisting essentially of cellulosic fibers and having a density from about 0.03 to about 0.14 g/cc and underlying said facing sheet, said first layer having top and bottom surfaces;

a second layer consisting essentially of cellulosic fibers, formed substantially separately from and underlying at least a portion of said first layer, said second layer having top and bottom surfaces, a density from about 0.14 to about 0.3 g/cc, a total void volume greater than about 80%, an average pore size distribution generally less than the average pore size distribution of said first layer and wherein there is an overlap in the pore size distributions of said first and second layers such that the smallest pores in said first layer are smaller than the largest pores in said second layer; and front and rear fluid storage pouches comprising superabsorbent material disposed in a hydrophilic web, said pouches being located underlying said first layer and spaced from one another at said opposed longitudinal ends, respectively of said absorbent structure.

2. The invention of claim 1 wherein said front and rear fluid storage pouches are respectively disposed at the front one-third and rear one-third of said absorbent structure.

3. The invention of claim 2 wherein said absorbent structure is substantially free of superabsorbent material in the middle one-third thereof.

4. The invention of claim 1, wherein said second layer comprises hardwood fibers.

5. The invention of claim 3 wherein said front and rear fluid storage pouches overlay said second layer and are in fluid conductive contact with said bottom surface of said first layer.

6. The invention of claim 3 wherein said front and rear fluid storage pouches underlay said second layer and are in fluid conductive contact with said bottom surface of said second layer.

7. The invention of claim or 5 wherein said fluid storage pouches each have a density greater than or equal to the density of said first layer and less than or equal to the density of said second layer.

8. The invention of claim 7 wherein said fluid storage pouches comprise nonwoven webs.

9. The invention of claim 8 wherein said fluid storage pouches comprise a melt blown web.

10. The invention of claim 1, further comprising a third layer of cellulosic fibers, said third layer having the same density range as said second layer and underlying said second layer.

11. The invention of claim 1, wherein the density of said first layer is from about 0.07 to about 0.11 g/cc.

12. The invention of claim 1, wherein the density of said second layer is from about 0.16 to about 0.22 g/cc.

13. The invention of claim 1, wherein the density of said first layer is from about 0.07 to about 0.11 g/cc and the density of said second layer is from about 0.16 to about 0.22 g/cc.

14. The invention of claim 1, wherein said first layer comprises softwood fibers.

15. The invention of claim 14 wherein said first layer comprises preponderantly softwood fibers.

16. The invention of claim 15 wherein said first layer comprises predominantly softwood fibers.

17. The invention of claim 4 wherein said second layer comprises preponderantly hardwood fibers.

18. The invention of claim 17 wherein said first layer comprises predominantly hardwood fibers.

19. The invention of claim 15 wherein said second layer comprises hardwood fibers.

20. The invention of claim 16 wherein said second layer comprises hardwood fibers.

21. The invention of claim 14 wherein said second layer comprises preponderantly hardwood fibers.

22. The invention of claim 15 wherein said second layer comprises preponderantly hardwood fibers.

23. The invention of claim 16 wherein said second layer comprises preponderantly hardwood fibers.

24. The invention of claim 14 wherein said second layer comprises predominantly hardwood fibers.

25. The invention of claim 15 wherein said second layer comprises predominantly hardwood fibers.

26. The invention of claim 16 wherein said second layer comprises predominantly hardwood fibers.

27. The invention of claim 1, 2, 3 or 5, wherein said body-facing sheet comprises at least two nonwoven web components, including a soft, compressible fluid transfer layer of synthetic fibers in fluid conductive contact with a bodyside top liner of synthetic fibers.

28. The invention of claim 27 wherein said second layer comprises hardwood fibers.

29. The invention of claim 27 wherein said first layer comprises softwood fibers and said second layer comprises hardwood fibers.

30. The invention of claim 27, wherein at least one of said components, comprise a carded, airlaid or spunbonded web of synthetic fibers.

31. The invention of claim 30, wherein at least one of said components comprise polyolefin or polyester fibers.

32. The invention of claim 27, wherein said body-facing sheet has a basis weight in the range from about 30–40 g/m² and a thickness from about 0.1 to about 1.0 cm.

33. The invention of claim 32, wherein the basis weight of said body-facing sheet is from about 30 to about 100 g/m².

34. The invention of claim 27, wherein the basis weight of said top liner is from about 10 to 15 g/m² and the basis weight of said transfer layer is from about 20 to 90 g/m².

35. The invention of claim 32, wherein the synthetic fibers of said transfer layer and top liner contain an effective amount of surfactant or other finish to render said fibers wettable.

36. The invention of claim 32, wherein at least one of said components comprise a carded, airlaid or spunbonded web of synthetic fiber.

37. The invention of claim 36, wherein said transfer layer comprises polyolefin fibers.

38. The invention of claim 36, wherein said transfer layer contains from about 25 to about 50% weight hollow polyester staple fibers.

39. The invention of claim 37, wherein said synthetic fibers of said transfer layer comprise more than about 50% weight polypropylene fibers.

40. The invention of claim 36, wherein said transfer layer contains from about 25 to about 50 weight % polyester staple fibers from about 3-6 denier and about 1-2 inches in length.

41. The invention of claim 35, wherein said transfer layer and top liner contain from about 0.2 to 0.5% weight surfactant.

42. The invention of claim 37, wherein at least one of said components comprise a spunbonded web.

43. The invention of claim 27, wherein said transfer layer is formed from a nonwoven web of filaments spun and collected without bonding which transfer layer is then bonded or otherwise joined to said top liner.

44. The invention of claim 43, wherein said transfer layer is bonded to said top liner by thermal or ultrasonic bonds.

45. The invention of claim 43, wherein said transfer layer comprises polyolefin fibers having a denier in the range of about 3-6 denier.

46. The invention of claim 27 wherein said first layer has a density from about 0.07 to about 0.11 g/cc and wherein said second layer has a density from about 0.16 to about 0.22 g/cc.

47. The invention of claim 27 wherein said first layer comprises softwood fibers.

48. In a disposable absorbent garment, an absorbent structure having opposed longitudinal ends, a central crotch portion and including a bodyfacing sheet, a backing sheet and liquid absorbing material therebetween, said liquid absorbing material comprising:
  a first layer comprising softwood fibers and having a density from about 0.03 to about 0.14 grams per cubic centimeter and underlying said facing sheet, said first layer having top and bottom surfaces;
  a second layer comprising hardwood fibers formed substantially separately from and underlying at least a portion of said first layer, said second layer having top and bottom surfaces, a density from about 0.14 to about 0.3 grams per cubic centimeter, a total void volume greater than about 80%, an average pore size distribution generally less than the average pore size distribution of said first layer and wherein there is an overlap in the pore size distributions of said first and second layers such that the smallest pores in said first layer are smaller than the largest pores in said second layer; and
  front and rear fluid storage pouches comprising superabsorbent material disposed in a hydrophilic web, said pouches being located underlying said first layer and spaced from one another at said opposed longitudinal ends, respectively of said absorbent structure.

* * * * *